United States Patent [19]

Chang et al.

[11] Patent Number: 5,175,375
[45] Date of Patent: Dec. 29, 1992

[54] SELECTIVE ORTHO PROPYLATION OF PHENOL OVER LARGE PORE ZEOLITE

[75] Inventors: Clarence D. Chang, Princeton, N.J.; Stuart D. Hellring, Yardley, Pa.

[73] Assignee: Mobil Oil Corporation, Fairfax, Va.

[21] Appl. No.: 774,959

[22] Filed: Oct. 11, 1991

[51] Int. Cl.$^5$ .................. C07C 39/06; C07C 37/14; C07C 37/16

[52] U.S. Cl. .................. 568/781; 568/786; 568/789; 568/791; 568/793; 568/794

[58] Field of Search ............... 568/781, 791, 793, 786, 568/789, 780, 794

[56] References Cited

U.S. PATENT DOCUMENTS

| | | | |
|---|---|---|---|
| 3,968,173 | 7/1976 | Klein et al. | 568/781 |
| 4,197,413 | 4/1980 | Kaeding et al. | 568/798 |
| 4,205,189 | 5/1980 | Young et al. | 568/763 |
| 4,283,573 | 8/1981 | Young | 568/794 |
| 4,391,998 | 7/1983 | Wu | 568/781 |
| 4,393,262 | 7/1983 | Kaeding | 585/467 |
| 4,405,818 | 9/1983 | Stead et al. | 568/781 |
| 5,030,770 | 10/1991 | Wimmer et al. | 568/781 |
| 5,072,054 | 12/1991 | Marler et al. | 568/794 |

Primary Examiner—Werren B. Lone
Attorney, Agent, or Firm—Alexander J. McKillop; Charles J. Speciale; Marina V. Schneller

[57] ABSTRACT

The invention relates to producing ortho isopropyl phenol catalytically by contacting phenol with isopropanol or propylene, at a temperature of from about 200° C. to about 300° C., with ZSM-12 and zeolite Beta; and recovering ortho isopropyl phenol.

16 Claims, 2 Drawing Sheets

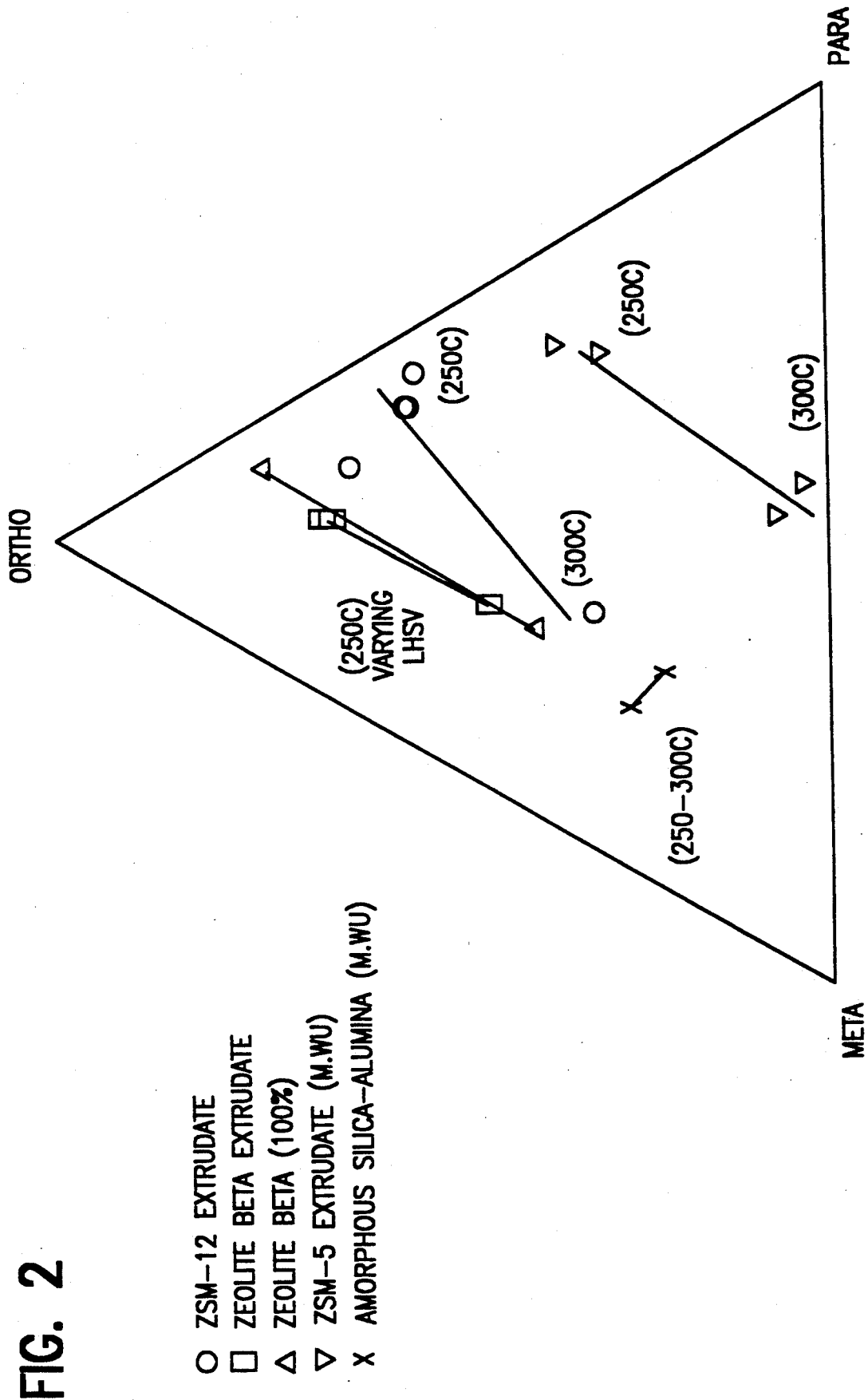

SELECTIVE ORTHO PROPYLATION OF PHENOL OVER LARGE PORE ZEOLITE

FIELD OF THE INVENTION

The invention relates to catalytic propylation of phenol which exhibits high selectivity for ortho-isopropylphenol, with minimal selectivity for normal propylphenol products. Selectivity for ortho-isopropylphenol can exceed 70. The catalyst for the catalytic propylation is a large pore zeolite, preferably ZSM-12 or zeolite beta.

The ortho selectivity of the catalysis of the invention is different from the selectivity of other zeolite catalyzed phenol alkylations. Surprisingly, these large pore zeolites also give much higher ortho-selectivity than does amorphous silica-alumina under similar conditions. In addition, alkylation activity is higher with the large pore size zeolites compared to the amorphous silica-alumina catalyst.

BACKGROUND OF THE INVENTION

Alkylphenols find important uses as antioxidants in the fuels, lube, and polymer industries. Isopropylphenols also serve as intermediates for dihydroxybenzenes. Their preparation by alkylation of phenols has been undertaken.

Para-selective alkylation of phenols over the zeolite ZSM-5 has been reported in U.S. Pat. No. 4,391,998.

Naturally occurring and synthetic zeolites have been demonstrated to exhibit catalytic properties for various types of hydrocarbon conversions. Certain zeolites are ordered porous crystalline aluminosilicates having definite crystalline structure as determined by X-ray diffraction studies. Such zeolites have pores of uniform size which are uniquely determined by unit structure of the crystal. The zeolites are referred to as "molecular sieves" because the uniform pore size of a zeolite material may allow it to selectively absorb molecules of certain dimensions and shapes.

By way of background, one authority has described the zeolites structurally, as "framework" aluminosilicates which are based on an infinitely extending three-dimensional network of $AlO_4$ and $SiO_4$ tetrahedra linked to each other by sharing all of the oxygen atoms. Furthermore, the same authority indicates that zeolites may be represented by the empirical formula

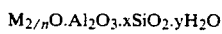

In the empirical formula, M was described therein to be sodium, potassium, magnesium, calcium, strontium and/or barium; x is equal to or greater than 2, since $AlO_4$ tetrahedra are joined only to $SiO_4$ tetrahedra, and n is the valence of the cation designated M; and the ratio of the total of silicon and aluminum atoms to oxygen atoms is 1:2. D. Breck, ZEOLITE MOLECULAR SIEVES, John Wiley & Sons, New York p. 5 (1974).

The term "crystalline" used to refer to these materials relates to the ordered definite crystalline structure of the material which is unique and thus identifiable by a characteristic X-ray diffraction pattern.

The term "microporous" as it refers to such material relates to pores, or channels, with diameters of less than 20 Angstroms. Examples of these microporous crystalline materials include crystalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOs and SAPOs, have pores of uniform size and channel systems which are uniquely determined by unit structure of the material. The uniform pore size and/or channel systems allow such a material to selectively absorb molecules of certain dimensions and shapes. In the art, microporous material having pores, or channels, of less than 20 Angstroms, can be divided into small, medium and large pore by the diameters of those pores, or channels. The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical.

Alternatively, the demarcation between small, medium, and large pore materials can be based on the following sorption properties (measured at room temperature for crystallites having a minimum dimension of 0.1 micron):

1. Small pore: $n-C_6/i-C_6$ sorption ratio greater than approximately 10.
2. Medium pore: $n-C_6/i-C_6$ is less than 10 and $n-C_6$/Mesitylene sorption ratio greater than approximately 5.
3. Large pore: $n-C_6$/Mesitylene sorption ratio less than approximately 5.

The prior art describes a variety of synthetic zeolites. These zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No., 3,314,752); zeolite ZSM-11 (U.S. Pat. No. 3,709,979) and zeolite ZSM-23 (U.S. Pat. No. 3,076,842), merely to name a few.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-22 is described in U.S. patent application Ser. No. 373,451 filed Apr. 30, 1982, and now pending. The entire description thereof is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 is more particularly described in U.S. Pat. No. 4,375,573. Such a description includes the X-ray diffraction pattern for ZSM-48.

Zeolite beta is more particularly described in U.S. Pat. Nos. 3,308,069 and Re. 28,341, each of which is relied upon and incorporated by reference herein.

Zeolite Y can be synthesized with an $SiO_2/Al_2O_3$ ratio up to about 5:1; in order to achieve higher ratios of $SiO_2/Al_2O_3$, various techniques have been developed to remove structural aluminum therefrom.

Crystalline ZSM-5 and its preparation are described in U.S. Pat. No. 3,702,886, the entire disclosure of which is incorporated herein by reference. It has a distinctive X-ray diffraction pattern which identifies it from other known crystalline silicates. A crystalline silicate composition having the structure of ZSM-5 is described in U.S. Pat. No. 29,948, the entire disclosure of which is incorporated herein by reference.

The incorporation of the identified patents and patent applications should not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material. The crystal structure of known zeolites may include framework elements, other than or in addition to silicon and aluminum, without changing its identification by the X-ray diffraction "fingerprint"; and these gallium, boron, iron and chromium containing silicates and aluminosilicates may be useful, or even preferred, in some applications described herein.

The silicon/aluminum atomic ratio of a given zeolite is often variable. For example, zeolite X can be synthesized with silicon/aluminum atomic ratios of from 1 to 1.5, while that ratio in zeolite Y is from 1.5 to 5. In some zeolites, the upper limit of the silicon/aluminum atomic ratio is unbounded. ZSM-5 is one such example wherein the silicon/aluminum atomic ratio is at least 2.5 and up to infinity. U.S. Pat. No. 3,941,871, reissued as RE. 29,948, discloses a porous crystalline silicate made from a reaction mixture containing no deliberately added aluminum and exhibiting the X-ray diffraction pattern characteristic of ZSM-5.

The exact chemical make-up of zeolites including ZSM-5 can determine the nature of its activity in a particular catalysis. In the art, zeolites are a subclass of crystalline microporous silicates. Zeolites can contain aluminum as well as silicon. The chemical make-up of the zeolite, in terms of its silica/alumina atomic ratio is of practical significance. In some zeolites, the upper limit of the silicon/aluminum atomic ratio is unbounded. ZSM-5 is one such example wherein the silicon/aluminum atomic ratio is at least 2.5 and up to infinity. By way of illustration, U.S. Pat. No. 3,941,871, reissued as RE 29,948, discloses a porous crystalline silicate made from a reaction mixture containing no deliberately added aluminum and exhibiting the X-ray diffraction pattern characteristic of ZSM-5 zeolites.

Zeolites can be acidic or non-acidic, depending on the framework aluminum content and on the amount of compensating cations, such as $Na^+$, $K^+$, etc.

SUMMARY OF THE INVENTION

In accordance with the present invention, product mixtures containing especially high concentrations of the ortho-isomer of isopropylated phenolic compounds are formed by alkylating phenol with either isopropyl alcohol or propylene. Such an alkylation reaction is carried out by contacting phenol and alkylating agent in the presence of a crystalline zeolite catalyst which is ZSM-12 or zeolite beta, in which the zeolite is in acid form. Alkylation is conducted under alkylation conditions which include a temperature of from about 200°–300° C.

DESCRIPTION OF THE DRAWING(S)

FIG. 2 is a graph of the relative production of ortho propylated phenols over various catalysts.

DETAILED DESCRIPTION OF THE INVENTION

Figure 1:
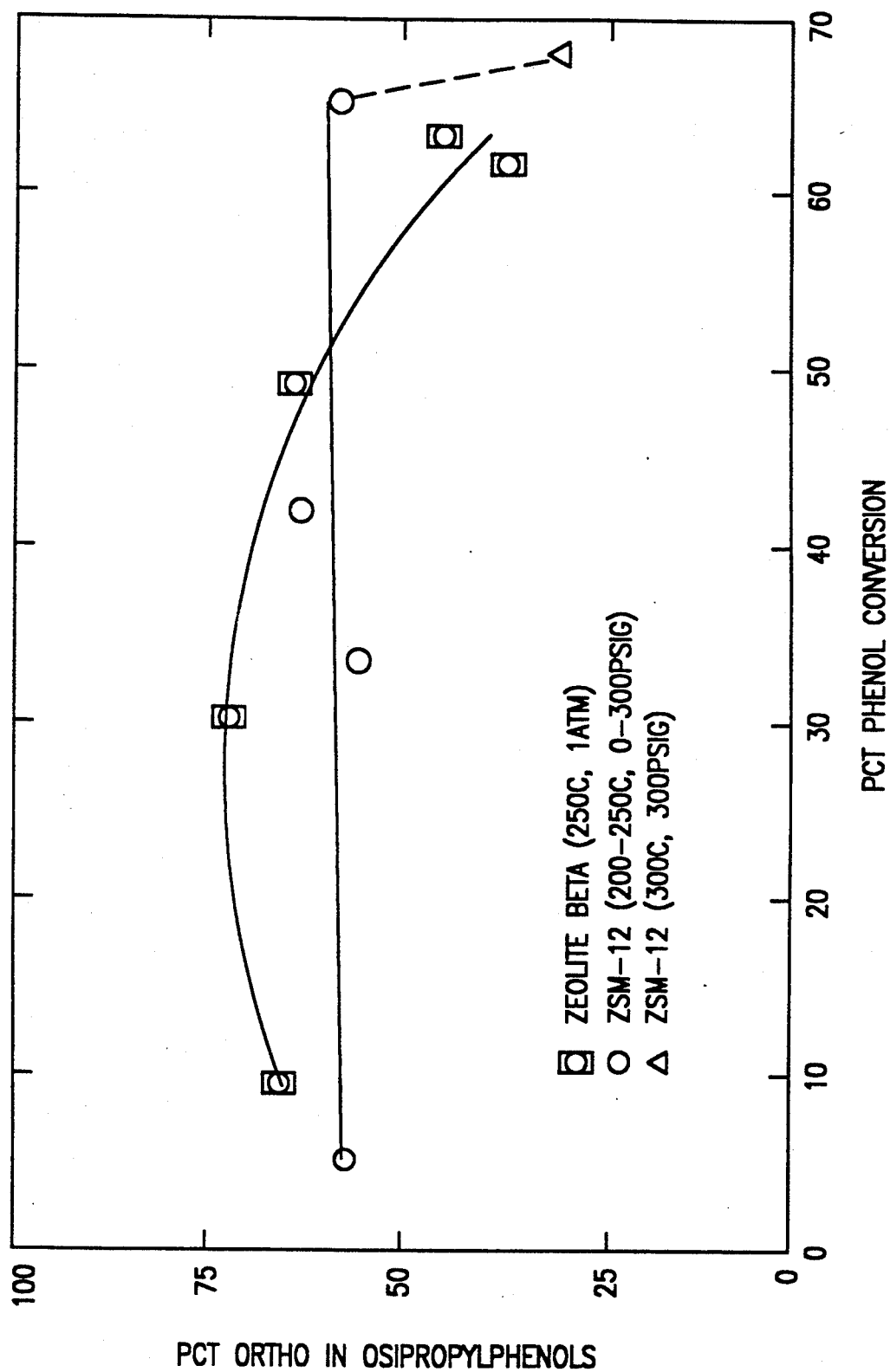
FIG. 1 is a graph, relating to isopropylation of phenol over large pore zeolites and is a plot of percent ortho isomer in isopropyl phenols vs. percent phenol conversion.

Phenol is selectively alkylated in accordance with the process of the invention. Alkylation is carried out by contacting phenol with alkylating agent, and the particular alkylating agent used in the process of the present invention is one which provides the ortho-isopropyl isomer of the phenol being alkylated. Thus the alkylating agent used herein is selected from isopropyl alcohol and propylene and is employed in a molar ratio of phenol to alkylating agent of from about 0.5:1 to 20:1, preferably from about 1:1 to 5:1. The isopropyl alcohol or propylene alkylating agent may be utilized as a pure compound or may be admixed with one or more inert diluents as noted below.

Alkylation to produce isopropyl phenolic compounds is conducted in the present process in the presence of an ortho-selective zeolite catalyst. These zeolites are ZSM-12 and zeolite Beta. Although these zeolites have unusually low alumina content, i.e. high silica to alumina ratios, they are very active even when the silica to alumina ratio exceeds 30. The activity is surprising since catalytic activity use to be attributed to framework aluminum atoms and/or cations associated with these aluminum atoms. In fact in the examples below the species of zeolite have silica:alumina molar ratios which exceed 100. The zeolites are used in protonated form; it is noted that the phrases, hydrogen form, protonated form, or acid form, relating to zeolites, are used interchangeably in the art.

Calcination of the ammonium exchanged form of the zeolite will produce the crystalline silicate or zeolite in its acid form (or protonated or hydrogen form). Calcination can be effected at temperatures up to about 600° C. Exchange of the crystalline silicate materials can be conducted to effect ammonium exchange at acidic sites of said materials. The source of the ammonium ion is not critical; thus the source can be ammonium hydroxide or an ammonium salt such as ammonium nitrate, ammonium sulfate, ammonium chloride and mixtures thereof. These reagents are usually in aqueous solutions; by way of illustration, aqueous solutions of 1N $NH_4OH$, 1N $NH_4NO_3$, 1N $NH_4Cl$ and 1N $NH_4Cl/NH_4OH$ have been used to effect ammonium ion exchange on these, and similar materials. The pH of the ion exchange is not critical but generally maintained at 7 to 12. Ammonium exchange may be conducted for a period of time ranging from about 0.5 to about 20 hours at a temperature ranging from ambient up to about 100° C. The ion exchange may be conducted in multiple stages.

As in the case of many catalysts, it can be desirable to incorporate the ZSM-12 or zeolite beta with another material resistant to the temperatures and other conditions employed in certain organic conversion processes. Such matrix materials include active and inactive materials and synthetic or naturally occurring zeolites as well as inorganic materials such as clays, silica and/or metal oxides, e.g. alumina. The latter may be either naturally occurring or in the form of gelatinous precipitates, sols or gels including mixtures of silica and metal oxides. Use of a material in conjunction with the zeolite ZSM-5, i.e. combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline silicate materials have been incorporated into naturally occurring clays, e.g. bentonite and kaolin. These materials, i.e. clays, oxides, etc., function, in part, as binders for the catalyst. It is desirable to provide a catalyst having good physical strength, because in petroleum refinery processing, the catalyst is often subjected to conditions which tend to break the catalyst down into powder-like materials which cause problems in processing.

Naturally occurring clays which can be composited with the hereby synthesized zeolite ZSM-5 include the montmorillonite and kaolin families which include the sub bentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolite ZSM-12 or zeolite Beta containing catalyst hereby synthesized can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of finely divided crystalline silicate and inorganic oxide gel matrix vary widely with the crystalline silicate content ranging from about 0.1 to about 90 percent by weight, and more usually in the range of about 10 to about 70 percent by weight of the composite.

Ortho-selective alkylation is accomplished by contacting the phenol reactant with the propylene or isopropyl alcohol alkylating agent in the presence of the zeolite catalyst under alkylation conditions. Alkylation conditions for the process herein essentially include a temperature between about 200° C. and 300° C., preferably from about 250° C. and 300° C. At temperatures in excess of 300° C., selectivity of the reaction may drop off.

Other reaction conditions include utilizing a feed weight hourly space velocity (WHSV) of between about 0.5 and about 100, preferably between about 1 and about 40. The reaction generally takes place at atmospheric pressure; but the pressure may be within the approximate range of zero (0) to 600 psig.

In addition to the phenol and propylene or isopropyl alcohol reactants, the reaction mixture may optionally contain various inert diluents to facilitate practice of the process. Common inert diluents can include water, air, nitrogen, carbon dioxide, lower alkanes and the like. Such diluents can comprise from about 0 up to about 50% by weight of the alkylation reaction mixture.

The process of this invention may be conducted with the organic reacts in either the gaseous or the liquid phase or both. It may be carried out as a batch-type, semi-continuous or continuous operation utilizing a fixed, fluidized, or moving bed catalyst system.

The following examples will serve to illustrate the process of this invention but are not limiting thereof.

EXAMPLES

EXPERIMENTAL

Propylations were conducted using a 61 wt.% phenol in isopropyl alcohol solution (mol phenol/mol isopropanol = 1). Isopropyl alcohol solutions were chosen over propylene alkylations to avoid using a preheated pumping system to feed molten phenol.

Propylations were run in typical stainless steel fixed-bed reactors (0.25in OD × 0.035in wall). Catalyst beds (6 ml) were zoned by vycor. Material balances exceeded 95%. Hydrocarbon products were analyzed by gc using a DB-1 capillary column (60m × 0.25mm ID; 0.1 μm film). Isopropylphenol regioisomers were separated using an 80/120 ⅛ in). ZSM-12 was used as an alumina extrudate (65% zeolite; $SiO_2/Al_2O_3 = 250$). Zeolite beta was used either as the pure zeolite or the alumina extrudate (50%). Product distributions are found in Tables 1 and 2.

TABLE 1

| Phenol Propylation over ZSM-12 | | | | | |
|---|---|---|---|---|---|
| Feed: 61 wt. % Phenol in Isopropyl alcohol | | | | | |
| TEMPERATURE (°C.) | 200 | 250 | 250 | 250 | 300 |
| PRESSURE (psig) | 300 | 300 | 300 | 0 | 300 |
| LHSV | 2 | 2 | 4 | 2 | 2 |
| PRODUCT DISTRIBUTION (wt %) | | | | | |
| Propylene | 1.83 | 0.88 | 1.61 | 1.80 | 0.30 |
| Isopropyl ether | 5.92 | 0.39 | 1.02 | 0.06 | 0.00 |
| Isopropyl alcohol | 20.37 | 0.30 | 0.49 | 0.09 | 0.00 |
| Phenol | 58.17 | 22.11 | 40.32 | 35.31 | 18.66 |
| Isopropylphenols | 1.75 | 56.97 | 41.16 | 46.84 | 57.91 |
| Isopropylphenyl ether | 11.40 | 0.45 | 3.13 | 0.10 | 0.22 |
| Isopropylphenyl-isopropyl ether | 0.10 | 0.30 | 0.98 | 0.00 | 0.00 |
| Diisopropyl phenols | 0.07 | 14.59 | 9.14 | 15.39 | 18.38 |
| Other products | 0.39 | 4.02 | 2.15 | 0.41 | 4.53 |
| NORMALIZED ISOPROPYLPHENOLS | | | | | |
| Ortho | 60.97 | 61.64 | 61.18 | 65.58 | 31.85 |
| Meta | 4.96 | 7.12 | 7.35 | 10.27 | 41.70 |
| Para | 34.06 | 31.24 | 31.47 | 24.16 | 26.45 |
| PHENOL CONVERSION | 5 | 64 | 34 | 42 | 69 |

TABLE 2

| Phenol Propylation over Zeolite Beta | | | | | |
|---|---|---|---|---|---|
| Feed: 61 wt. % Phenol in Isopropyl Alcohol | | | | | |
| TEMPERATURE (°C.) | 200 | 250 | 250 | 250 | 300 |
| PRESSURE (atm) | 1 | 1 | 1 | 1 | 1 |
| LHSV | 2 | 4 | 8 | 4 | 8 |
| PCT. ZEOLITE | 50 | 50 | 50 | 100 | 100 |
| PRODUCT DISTRIBUTION (wt %) | | | | | |
| Propylene | 1.23 | 1.36 | 1.70 | 1.33 | 1.83 |
| Isopropyl ether | 0.00 | 0.00 | 0.10 | 0.00 | 0.00 |
| Isopropyl alcohol | 0.44 | 0.24 | 5.24 | 0.04 | 0.00 |
| Phenol | 22.41 | 31.17 | 54.92 | 23.48 | 42.81 |
| Isopropylphenols | 45.47 | 43.90 | 27.19 | 49.99 | 41.73 |
| Isopropylphenyl ether | 0.00 | 0.00 | 1.32 | 0.01 | 0.07 |

TABLE 2-continued

| Phenol Propylation over Zeolite Beta | | | | | |
|---|---|---|---|---|---|
| Isopropylphenyl-isopropyl ether | 0.10 | 0.04 | 0.23 | 0.04 | 0.00 |
| Diisopropyl phenols | 28.56 | 22.94 | 9.16 | 24.55 | 13.50 |
| Other products | 1.78 | 0.35 | 0.14 | 0.57 | 0.06 |
| NORMALIZED ISOPROPYLPHENOLS | | | | | |
| Ortho | 44.83 | 66.08 | 66.88 | 39.60 | 73.87 |
| Meta | 33.49 | 13.81 | 13.53 | 18.30 | 6.13 |
| Para | 21.68 | 20.11 | 19.59 | 22.10 | 19.99 |
| PHENOL CONVERSION | 63 | 49 | 10 | 62 | 30 |

As can be seen from Table 1 and Table 2, as well as the figures of Drawings, high ortho-selectivity is obtained with either ZSM-12 or zeolite beta when phenol conversion is below 50% (FIG. 1). Under conditions sufficient to raise phenol conversion (i.e. increased contact time or temperature), the concentration of meta-isomer increases at the expense of ortho-isomer (FIG. 2).

Para-selectivity remains fairly constant even near 70% phenol conversion. The highest ortho-selectivity is observed with zeolite beta and approaches 75% at about 30% conversion.

These results differ considerably from those reported with ZSM-5, as described in U.S. Pat. No. 4,391,998. Under similar conditions (250.C, 20% conversion), ZSM-5 gave 54% para-isomer in the isopropylphenols, and only 32% ortho. At 300° C. (20% conversion), the ortho-isomer dropped to only 3-5%. Again the para-selectivity remained constant at this higher temperature, and the lost ortho-isomer resulted only in increased meta-isomer (43-44%).

Surprisingly, the ortho-selectivity found with these large-pore zeolites also exceeds that found with amorphous silica-alumina, as described in U.S. Pat. No. 4,391,998. At 250° C. (37% conversion), the latter catalyst gives only about 25% ortho-product. The major isomer from the amorphous material is meta (50%), despite this low conversion. Product distributions, therefore, approaches equilibrium.

Several studies focused on the homogeneous gas-phase alkylation of phenol with propyl cation reveal that ortho-isopropylphenol is the major product, C. F. (a) Attina, M.; Cacace, F.; Ciranni, G.; and Giacomella, P. J.C.S. Perkins II 1979,891; (b) Attina, M. and Giacomello, P. J. Am. Chem. Soc. 1979, 101, 6040. This is rationalized by initial O-alkylation of phenol to form an intermediate isopropylphenyloxonium cation, which then decomposes intramolecularly to the ortho-arenium ion. Ortho-selectivity in the gas-phase is reported as high as 80%. Para-isomer is formed mainly by intermolecular alkylation either directly or via alkyl transfer from the oxonium intermediate.

The unrestricted environment of these large-pore ZSM-12 and beta zeolites apparently allows the kinetic product to effuse efficiently. Sufficient channel volume to permit intramolecular rearrangement of the oxonium intermediate also appears to exist. In ZSM-5, an intermediate pore size zeolite, either or both of these processes are restricted and intermolecular propylation to the para-isomer dominates.

Although restrictions to effusion from the surface sites of amorphous silica-alumina should be minimal, the meta-isomer dominates with this catalyst.

Selectivity to diisopropylphenols appear somewhat higher for these large pore zeolites, although quantitative comparison is difficult from the reported data.

Since one likely source of meta-isomer is dealkylation of diisopropylphenols, differences in concentrations of the latter could have a bearing on observed regioselectivity. Certainly, mono-/di-propylation selectivity is expected to improve with phenol-rich feeds.

High concentrations of n-propylphenols are also reported for ZSM-5, but these isomers were minimal with ZSM-12 or zeolite beta. This again demonstrates the unique product selectivity obtained in an unrestricted channel structure.

Thus it is apparent that there has been provided, in accordance with the invention, a process which is a catalytic alkylation of phenol, that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A process for producing ortho isopropyl phenol, comprising
    contacting a feedstream, with a catalyst, at a temperature of from about 200° C. to about 300° C.,
        wherein the feedstream comprises phenol and at least one compound selected from the group consisting of isopropyl alcohol or propylene, and
        wherein the catalyst comprises a zeolite, in the hydrogen from,
        wherein the zeolite is selected from the group consisting of ZSM-12 and zeolite BETA; and
    recovering ortho isopropyl phenol.

2. The process of claim 1, wherein the temperature is from about 250° and 300° C.

3. The process of claim 1, wherein a feed weight hourly space velocity (WHSV) of between about 0.5 and about 100 is employed.

4. The process of claim 3, wherein a feed weight hourly space velocity (WHSV) ranges between about 1 and about 40.

5. The process of claim 3, wherein a pressure is employed which is in the range of zero (0) to 600 psig.

6. The process of claim 5 wherein the feed includes a diluent which can comprise from about 0 up to about 50% by weight of the feed.

7. The process of claim 5 wherein the catalyst is in the form of an extrudate.

8. A process for producing ortho isopropyl phenol, comprising
    contacting a feedstream, with a catalyst, at a temperature of from about 200° C. to about 300° C.,
        wherein the feedstream comprises phenol and at least one compound selected from the group consisting of isopropyl alcohol or propylene, and
        wherein the catalyst comprises a zeolite, in the hydrogen from,
        wherein the zeolite is selected from the group consisting of zeolite beta; and
    recovering ortho isopropyl phenol.

9. The process of claim 8, wherein the temperature is from about 250° and 300° C.

10. The process of claim 8, wherein a feed weight hourly space velocity (WHSV) of between about 0.5 and about 100 is employed.

11. The process of claim 10, wherein a feed weight hourly space velocity (WHSV) ranges between about 1 and about 40.

12. The process of claim 10, wherein a pressure is employed which is in the range of zero (0) to 600 psig.

13. The process of claim 12, wherein the feed includes a diluent which can comprise from about 0 up to about 50% by weight of the feed.

14. The process of claim 12, wherein the catalyst is in the form of an extrudate.

15. The process of claim 1, wherein the temperature is about 250° C.

16. The process of claim 9, wherein the temperature is about 300° C.

* * * * *

UNITED STATES PATENT AND TRADEMARK OFFICE
CERTIFICATE OF CORRECTION

PATENT NO. : 5,175,375
DATED : December 29, 1992
INVENTOR(S) : Pierre Chabardes et al It is certified that error appears in the above-indentified patent and that said Letters Patent is hereby corrected as shown below:

Claim 1, column 7, first five lines, formula 2 change " 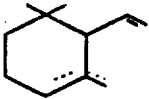 " to --  --.

Signed and Sealed this

Twenty-second Day of March, 1994

Attest:

BRUCE LEHMAN

Attesting Officer     Commissioner of Patents and Trademarks